(12) United States Patent
Nakazato et al.

(10) Patent No.: US 6,333,428 B1
(45) Date of Patent: Dec. 25, 2001

(54) 6-FLUOROBICYCLO[3.1.0]HEXANE DERIVATIVES

(75) Inventors: Atsuro Nakazato; Toshihito Kumagai; Kazunari Sakagami; Kazuyuki Tomisawa, all of Tokyo (JP)

(73) Assignee: Taisho Pharmaceutical Co., Ltd. (JP)

( * ) Notice: Subject to any disclaimer, the term of this patent is extended or adjusted under 35 U.S.C. 154(b) by 0 days.

(21) Appl. No.: 09/763,408
(22) PCT Filed: Jul. 26, 1999
(86) PCT No.: PCT/JP99/03984
§ 371 Date: Feb. 22, 2001
§ 102(e) Date: Feb. 22, 2001
(87) PCT Pub. No.: WO00/12464
PCT Pub. Date: Mar. 9, 2000

(30) Foreign Application Priority Data

Aug. 31, 1998 (JP) ............................................. 10-246343
Mar. 25, 1999 (JP) ............................................. 11-082607

(51) Int. Cl.[7] .............................................. C07C 69/74
(52) U.S. Cl. ........................ 560/116; 560/119; 560/122; 560/124; 560/125
(58) Field of Search ................................ 560/116, 119, 560/122, 124, 125

(56) References Cited

U.S. PATENT DOCUMENTS

| | | |
|---|---|---|
| 5,750,566 A | 5/1998 | Monn et al. ................. 514/510 |
| 5,912,248 A * | 6/1999 | Fernandez et al. |
| 5,916,920 A | 6/1999 | Fernandez et al. .......... 514/561 |
| 5,925,680 A | 7/1999 | Helton et al. ................ 514/574 |
| 5,925,782 A | 7/1999 | Monn .......................... 560/119 |
| 5,958,960 A * | 9/1999 | Massey et al. |
| 6,160,009 A | 12/2000 | Massey et al. .............. 514/510 |

FOREIGN PATENT DOCUMENTS

| | | |
|---|---|---|
| EP | 0 774 454 A1 | 11/1996 |
| EP | 0 774 455 A1 | 11/1996 |
| EP | 0 878 463 B1 | 5/1998 |
| EP | 0 928 792 A2 | 1/1999 |
| JP | 8-188561 | 7/1996 |
| JP | 11-255722 | 9/1999 |
| JP | 11-279129 | 10/1999 |
| WO | 97/17950 | 5/1997 |
| WO | 97/17952 | 5/1997 |
| WO | 99/38839 | 5/1999 |

* cited by examiner

Primary Examiner—Gary Geist
Assistant Examiner—Hector M. Reyes
(74) Attorney, Agent, or Firm—Lorusso & Loud

(57) ABSTRACT

The present invention provides fluorobicyclo[3.1.0]hexane derivatives represented by the formula

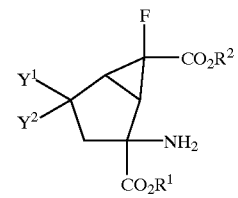

[wherein $R^1$ and $R^2$ are the same or different and each represents a hydrogen atom, a $C_{1-10}$ alkyl group, a $C_{3-8}$ cycloalkyl group or a $C_{3-8}$ cycloalkyl-$C_{1-5}$ alkyl group: $Y^1$ and $Y^2$ are the same or different and each represents a hydrogen atom, a $C_{1-10}$ alkylthio group, a $C_{3-8}$ cycloalkylthio group, a $C_{3-8}$ cycloalkyl-$C_{1-5}$ alkylthio group, a $C_{1-5}$ alkoxy group, a $C_{3-8}$ cycloalkoxy group or a $C_{3-8}$ cycloalkyl-$C_{1-5}$ alkoxy group; or one represents a hydrogen atom and the other represents a hydroxyl group, a $C_{1-5}$ alkoxy group, a $C_{3-8}$ cycloalkoxy group or a $C_{3-8}$ cycloalkyl-$C_{1-5}$ alkoxy group; or $Y^1$ and $Y^2$ together represent an oxygen atom or —X(CH$_2$)$_n$X— (X represents an oxygen atom or a sulfur atom: N is 2 or 3)], pharmaceutically acceptable salts thereof, or hydrates thereof.

The compounds of the present invention are useful as drugs, in particular group 2 metabotropic glutamate receptor agonists, and useful for treatment or prevention of psychiatric disorders such as, for example, schizophrenia, anxiety and associated diseases, depression, bipolar disorder, and epilepsy, as well as neurological diseases such as, for example, drug dependence, cognitive disorders, Alzheimer's disease, Huntington's chorea, Parkinson's disease, dyskinesia associated with muscular stiffness, cerebral ischemia, cerebral failure, myelopathy, and head trauma.

13 Claims, No Drawings

6-FLUOROBICYCLO[3.1.0]HEXANE DERIVATIVES

FIELD OF TECHNOLOGY

This invention relates to 6-fluorobicyclo[3.1.0]hexane derivatives that are useful as drugs. In particular, it relates to novel 2-amino-6-fluorobicyclo[3.1.0]hexane-2,6-dicarboxylic acid derivatives that are useful for the treatment and prevention of psychiatric disorders such as, for example, schizophrenia, anxiety and its associated diseases, depression, bipolar disorder and epilepsy; and neurological diseases such as drug dependence, cognitive disorders, Alzheimer's disease, Huntington's chorea, Parkinson's disease, dyskinesia associated with muscular stiffness, cerebral ischemia, cerebral failure, myelopathy, and head trauma.

BACKGROUND ART

In recent years, with the repeated cloning of glutamate receptor genes, it has become clear that there are surprisingly many subtypes of glutamate receptors. At present, glutamate receptors are roughly classified into two types: the "ionotropic type", in which the receptor has an ion channel type structure, and the "metabotropic type", in which the receptor is coupled to G-proteins. Ionotropic receptors are classified pharmacologically into three types: N-methyl-D-asparaginic acid (NMDA), α-amino-3-hydroxy-5-methyl isoxazole-4-propionate (AMPA), and kynate (Science, 258, 597–603, 1992). Metabotropic receptors are classified into eight types, type 1 through type 8 (J. Neurosci., 13, 1372–1378, 1993; Neuropharmacol., 34, 1–26, 1995).

The metabotropic glutamate receptors are classified pharmacologically into three groups. Of these, group 2 (mGluR2/mGluR3) bind with adenylcyclase, and inhibit the accumulation of the Forskolin stimulation of cyclic adenosine momophosphate (cAMP) (Trends Pharmacol. Sci., 14, 13(1993)), which suggests that compounds that act on group 2 metabotropic glutamate receptors should be useful for the treatment or prevention of acute and chronic psychiatric and neurological diseases. As substances that act on group 2 metabotropic glutamate receptors, (+)-(1S,2S,5R,6S)-2-aminobicyclo [3.1.0]hexane-2,6-dicarboxylic acid has been disclosed in Japanese Unexamined Patent Publication, First Publication No. Hei 8-188561 [1996]. And, (1S*,2S*,5R*,6R*)-2-amino-4-oxobicyclo[3.1.0]hexane-2,6-dicarboxylic acid, (1S*,2S*,4S*,5R*,6R*)-2-amino-4-hydroxybicyclo[3.1.0]hexane-2,6-dicarboxylic acid, and (1S*,2R*,4S*,5S*,6S*)-2-amino-4-flurobicyclo[3.1.0]hexane-2,6-dicarboxylic acid have been disclosed in EP-A-878,463.

Fluorine atoms tend to be strongly electron-attractive and to confer high fat solubility, so that compounds into which fluorine atoms are introduced greatly change their physical properties. Thus introducing fluorine atoms might greatly affect the absorbability, metabolic stability, and pharmacological effects of a compound. But it is by no means easy to introduce fluorine atoms. In fact, Japanese Unexamined Patent Publication, First Publication No. Hei 8-188561 [1996] does not even discuss the introduction of fluorine atoms into (+)-(1S,2S,5R,6S)-2-aminobicyclo[3.1.0] hexane-2,6-dicarboxylic acid. Further, (1S*,2R*,4S*,5S*,6S*)-2-amino-4-flurobicyclo[3.1.0]hexane-2,6-dicarboxylic acid which has been disclosed in EP-A-878,463 was prepared by merely a substitution of a hydroxyl group in (1S*,2S*,4S*,5R*,6R*)-2-amino-4-hydroxybicyclo[3.1.0] hexane-2,6-dicarboxylic acid, by a fluorine atom by use of normal fluorination agents.

DISCLOSURE OF THE INVENTION

In view of the aforementioned present state of the prior art, the purpose of this invention is to provide drugs that are effective for the treatment and prevention of psychiatric disorders such as, for example, schizophrenia, anxiety and its associated diseases, depression, bipolar disorder and epilepsy; and neurological diseases such as drug dependence, cognitive disorders, Alzheimer's disease, Huntington's chorea, Parkinson's disease, dyskinesia associated with muscular stiffness, cerebral ischemia, cerebral failure, myelopathy and head trauma; especially oral drugs that can act on group 2 metabotropic glutamate receptors.

The inventors of the present invention, who made a diligent study of 2-amino-6-fluorobicyclo[3.1.0]hexane-2,6-dicarboxylic acid derivatives in which a fluorine atom is introduced into the 6position of (+)-(1S,2S,5R,6S)-2-aminobicyclo[3.1.0]hexane-2,6-dicarboxylic acid, (1S*,2S*,5R*,6R*)-2-amino-4-oxobicyclo[3.1.0]hexane-2,6-dicarboxylic acid, and (1S*,2S*,4S*,5R*,6R*)-2-amino-4-hydroxybicyclo[3.1.0]hexane-2,6-dicarboxylic acid, have discovered novel 2-amino-4-flurobicyclo[3.1.0]hexane-2,6-dicarboxylic acid derivatives that when taken orally can affect group 2 metabotropic glutamate receptors, thereby completed this invention.

That is, the present invention relates to 6-fluorobicyclo [3.1.0]hexane-2,6-dicarboxylic acid derivatives represented by the formula [I]

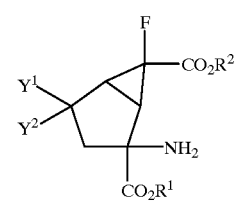

[I]

[wherein $R^1$ and $R^2$ are the same or different, and each represents a hydrogen atom, a $C_{1-10}$ alkyl group, a $C_{3-8}$ cycloalkyl group or a $C_{3-8}$ cycloalkyl-$C_{1-5}$ alkyl group: $Y^1$ and $Y^2$ are the same or different, and each represents a hydrogen atom, a $C_{1-10}$ alkylthio group, a $C_{3-8}$ cycloalkylthio group, a $C_{3-8}$ cycloalkyl-$C_{1-5}$ alkyl thio group, a $C_{1-5}$ alkoxy group, a $C_{3-8}$ cycloalkoxy group or a $C_{3-8}$ cycloalkyl-$C_{1-5}$ alkoxy group; or one represents a hydrogen atom and the other represents a hydroxyl group, a $C_{1-5}$ alkoxy group, a $C_{3-8}$ cycloalkoxy group or a $C_{3-8}$ cycloalkyl-$C_{1-5}$ alkoxy group; or $Y^1$ and $Y^2$ together represent an oxygen atom or —X(CH$_2$)$_n$X— group (X represents an oxygen atom or a sulfur atom: n is 2 or 3)], pharmaceutically acceptable salts thereof, or hydrates thereof.

In the present invention, the $C_{1-10}$ alkyl group means a straight-chain or branched-chain alkyl group, examples of which include a methyl group, an ethyl group, a propyl group, an isopropyl group, a butyl group, an isobutyl group, a t-butyl group, a pentyl group, an isopentyl group, a 1-ethylpropyl group, a hexyl group, an isohexyl group, a 1-ethylbutyl group, a heptyl group, an isoheptyl group, an octyl group, a nonyl group, and a decyl group. The $C_{3-8}$ cyclopropyl group means, for example, a cyclopropyl group, a cyclobutyl group, a cyclopentyl group, a cyclohexyl group, etc. The $C_{3-8}$ cycloalkyl-$C_{1-5}$ alkyl group means, for example, a cyclopropylmethyl group, a cyclobutylmethyl group, a cyclopentylmethyl group, a cyclohexylmethyl group, etc. The $C_{1-10}$ alkylthio group means a straight-chain or branched-chain alkylthio group, examples of which include a methylthio group, a ethylthio group, a propylthio group, an isopropylthio group, a butylthio group, an isobutylthio group, a t-bytylthio group, a pentylthio group, an isopentylthio group, a 1-ethylpropylthio group, a hexylthio group, an isohexylthio group, a 1-ethylbutylthio group, a heptylthio group, an isoheptylthio group, an octylthio group, a nonylthio group, and a decylthio group. The $C_{3-8}$ cycloalkylthio group means, for example, a cyclopropylthio group, a cyclobutylthio group, a cyclopentylthio group, a cyclohexylthio group, etc. The $C_{3-8}$ cycloalkyl-$C_{1-5}$ alkylthio group means, for example, a cyclopropylmethylthio group, a cyclobutylmethylthio group, a cyclopentylmethylthio group, a cyclohexylmethylthio group, etc. The $C_{1-5}$ alkoxy group means a straight-chain or branched chain alkoxy group, examples of which include a methoxy group, an ethoxy group, a propoxy group, an isopropoxy group, a butoxy group, an isobutoxy group, t-butoxy group, a pentoxy group, an isopentoxy group, and a 1-ethylpropoxy group. The $C_{3-8}$ cycloalkoxy group means, for example, a cyclopropoxy group, a cyclobutoxy group, a cyclopentoxy group, etc. The $C_{3-8}$ cycloalkyl-$C_{1-5}$alkoxy group means, for example, a cyclopropylmethoxy group, a cyclobutylmethoxy group, a cyclopropylethoxy group, etc.

As the pharmaceutically acceptable salt in this invention, one can cite, for example, a salt with an inorganic acid such as sulfuric acid, hydrochloric acid, and phosphoric acid; a salt with an organic acid such as acetic acid, oxalic acid, lactic acid, tartaric acid, fumaric acid, maleic acid, methanesulfonic acid and benzenesulfonic acid; a salt with an amine such as trimethylamine and methylamine; or a salt with a methyl ion such as sodium ion, potassium ion and calcium ion. The compounds of the present invention may exist as various solvates, but from the standpoint of applicability as a drug, hydrates are preferable.

In compounds represented by the formula [I], if both of $Y^1$ and $Y^2$ represent hydrogen atoms, or together represent an oxygen atom or —$X(CH_2)_nX$— (X is an oxygen atom or a sulfur atom: n is 2 or 3), or if both of $Y^1$ and $Y^2$ represent a $C_{1-10}$ alkylthio group, a $C_{3-8}$ cycloalkylthio group, a $C_{3-8}$ cycloalkyl-$C_{1-5}$ alkylthio group, a $C_{1-5}$ alkoxy group, a $C_{3-8}$ cycloalkoxy group or a $C_{3-8}$ cycloalkyl-$C_{1-5}$ alkoxy group, asymmetric carbon atoms are present in the positions of 1, 2, 5, and 6. Therefore, the compounds of the present invention of the above cases can exist as optically active substances, enantiomers thereof or racemic body thereof.

Further, if $Y^1$ and $Y^2$ differently represent a hydrogen atom, a $C_{1-10}$ alkylthio group, a $C_{3-8}$ cycloalkylthio group, a $C_{3-8}$ cycloalkyl-$C_{1-5}$alkylthio group, a $C_{1-5}$alkoxy group, a $C_{3-8}$cycloalkoxy group or a $C_{3-8}$ cycloalkyl-$C_{1-5}$ alkoxy group, or one of $Y^1$ and $Y^2$ represents a hydrogen atom and the other represents a hydroxyl group, a $C_{1-5}$ alkoxy group, a $C_{3-8}$ cycloalkoxy group or a $C_{3-8}$ cycloalkyl-$C_{1-5}$ alkoxy group, asymmetric carbon atoms are present in the positions of 1, 2, 4, 5, and 6. Therefore, the compounds of the present invention of the above cases can be as optically active substances, enantiomers thereof, racemic body or a mixture of diastereomers based on $Y^1$ and $Y^2$ in the 4-position.

It is preferable that the compounds represented in the formula [I] have the following relative stereochemical configuration represented by the formula [I']:

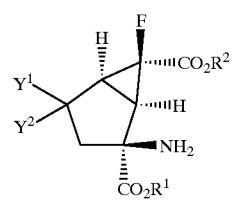

[I']

A (+) or (−)-(1R*,2S*,6S*)-2-amino-6-fluoro-4-substituted-bicyclo[3.1.0]hexane-2,6-dicarboxylic acid can be cited as a specific example of particularly preferable compounds in the formula [I'].

The other preferable combinations of $Y^1$ and $Y^2$ in the compounds represented by the formula [I] include the cases wherein both of them represent hydrogen atoms, wherein they together represent an oxygen atom, and wherein one of them represents an hydrogen atom and the other represents a hydroxyl group, each of which can be shown by the following formulas [II], [III] and [IV], respectively.

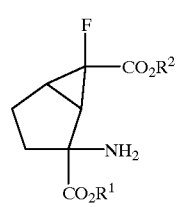

[II]

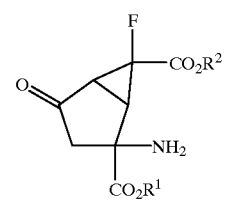

[III]

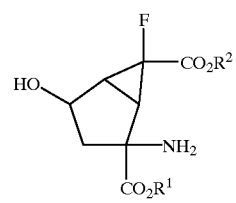

[IV]

Further, it is more preferable that the compounds of the above formulas [II], [III] and [IV] have the following relative stereochemical configurations represented by the formulas [II'], [III'] and [IV'], respectively.

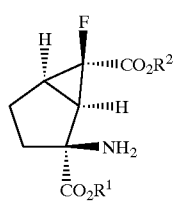

[II']

-continued

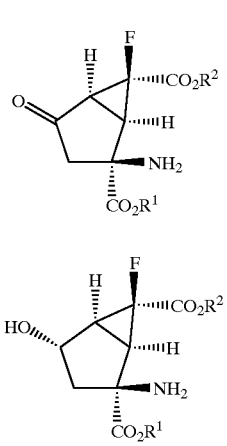

[III']

[IV']

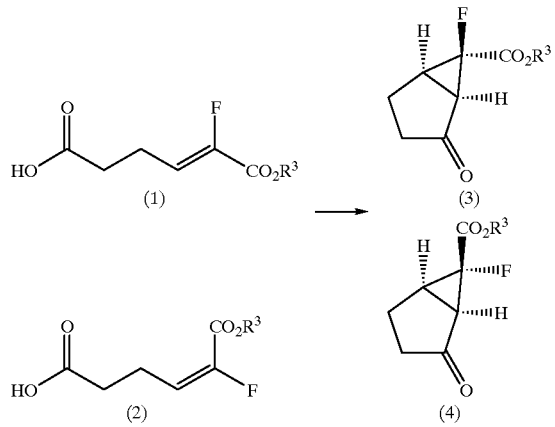

(−)-(1R*,2S*,5R*6R*)-2-amino-6-fluorobicyclo[3.1.0]
hexane-2,6-dicarboxylic acid, (+)-(1R*,2S*,5S*6S*)-2-
amino-6-fluoro-4-oxobicyclo[3.1.0]hexane-2,6-
dicarboxylic acid, and (+) or (−)-(1R*,2S*,4S*,5S*,6S*)-2-
amino-6-fluoro-4-hydroxybicyclo[3.1.0]hexane-2,6-
dicarboxylic acid, all of which are optically active
substances, can be cited as particularly preferable compounds among the compounds represented by the formulas [II'], [III'] and [IV'], respectively.

If in the formulas [I], [II], [III] and [IV] (including the cases of [I'], [II'], [III'] and [IV']) one or both of $R^1$ and $R^2$ represent something other than a hydrogen atom, that is, the ester forms will not have an effect on group 2 metabotropic glutamate receptors. But, these ester forms are hydrolyzed in vivo, and are transformed into a carboxylic acid, which does have an effect on group 2 metabotropic glutamate receptors. In this way, the ester forms of the compounds encompassed in the present invention are very useful because they function as prodrugs.

The compounds of the formula [I] can be manufactured according to the following reactions. In the following reaction formulas, $R^1$, $R^2$, $Y^1$ and $Y^2$ are the same as above, $R^3$ and $R^4$ represent $R^2$ and $R^1$ other than a hydrogen atom, respectively. X' represents a chlorine atom, a bromine atom or an iodine atom. $Y^3$ and $Y^4$ together represent —X(CH$_2$)$_n$X— (X is an oxygen atom or a sulfur atom: n is 2 or 3), or they identically or differently represent a $C_{1-10}$ alkylthio group, a $C_{3-8}$ cycloalkylthio group, a $C_{3-8}$ cycloalkyl-$C_{1-5}$ alkylthio group, a $C_{1-5}$ alkoxy group, a $C_{3-8}$ cycloalkoxy group or a $C_{3-8}$ cycloalkyl-$C_{1-5}$ alkoxy group. Ar represents an aryl group such as a phenyl group, a 4-chlorophenyl group and a 4-methoxyphenyl group. $Z^1$ represents a common protective group for a hydroxyl group. $Z^2$ represents a common protective group for a hydroxyl group, or represents a hydrogen atom. $Z^3$ represents a common protective group for an amino group. Common protective groups for hydroxyl and amino groups are described in detail in "Protective Groups in Organic Synthesis", by Theodora W. Greene and Peter G. M. Wuts, the contents of which are hereby incorporated by reference.

As shown in the above reaction formula, the racemic ketone (3) or (4), or a mixture of diastereomers of both can be obtained by, first, transforming a carboxylic acid moiety of the Z form (1) or E form (2) of the above fluoroacrylic acid derivative, or a mixture of both into an active form, and then reacting with diazomethane, followed by reaction in an inert solvent under the presence of a metal catalyst.

The active form herein means an acid halide or a mixed acid anhydride. The acid halide can be obtained by reacting common halogenation agents for a hydroxyl group in a carboxylic acid, such as, for example, thionyl chloride, oxalyl chloride and carbon tetrachloride-triphenylphosphine, with the Z form (1) or the E form (2) of the fluoroacrylic acid derivative, or with a mixture of both. The mixed acid anhydride can be obtained by reacting halo-carbonates such as isobutyl chlorocarbonate and ethyl chlorocarbonate, or organic acid anhydrides such as acetic acid anhydride and trifluoroacetic acid anhydride with the Z form (1) or the E form (2) of the fluoroacrylic acid derivative, or a mixture of both, with or without the presence of organic bases such as triethylamine, N-methylmorpholine, diisopropylethylamine and pyridine, or inorganic bases such as potassium carbonate, sodium hydrogen carbonate and sodium hydride.

The metal catalyst can, for example, be copper agents such as copper (I) iodide, copper (II) sulfate, copper (II) acetate, copper (II) bis(acetylacetonate) and copper (II) bis(N-t-butylsalicylaldiimidate); rhodium agents such as rhodium (II) acetate and rhodium (II) trifluoroacetate; and palladium agents such as palladium (II) acetate and bis (benzonitrile)dichloro palladium (II).

Examples of the inert solvent can include ethers such as tetrahydrofuran, dioxane and diethylether; hydrocarbons such as toluene and benzene; halogen type solvents such as methylene chloride, chloroform and 1,2-dichloroethane; N,N-dimethylformamide; and acetonitrile.

The racemic ketone (3) or the racemic ketone (4) can be directly optically resolved by use of the HPLC method employing chiral carriers such as cellulose carbamate derivatives and amylosecarbamate derivatives. They can also be optically resolved by being changed into slats with optically active amines such as (+) or (−)-1-phenylethylamine, (+) or (−)-2-amino-1-butanol, (+) or (−)-alaninol, brucine, cinchonidine, cinchonine, quinine, quinidine and dehydroabiethylamine, after an ester moiety of the racemic ketone (3) or the racemic ketone (4) is transformed into a carboxylic acid under normal hydrolysis conditions. Further, they can be resolved after being changed into amido forms by use of a primary or secondary optical active amines such as (+) or (−)-1-phenylethylamine, (+) or (−)-2-amino-1-butanol, (+) or (−)-alaninol, and normal amidation agents such as dicyclohexylcarbodiimide (DCC).

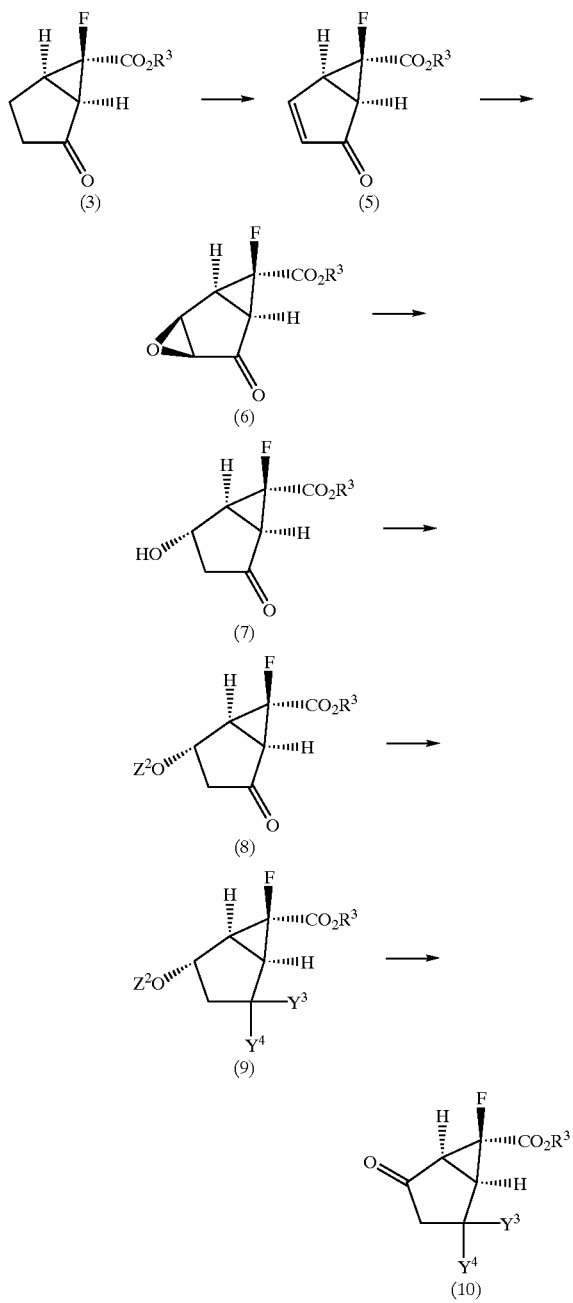

As shown in the above reaction formula, the ketone (3), which is present as an optically active substance, enantiomer or racemic body, can be transformed into the enone (5), which is present as an optically active substance, enantiomer or racemic body, by reacting it with, for example, silylation agents under the presence of bases to form the silylenolether followed by reacting it with, for example, palladium (II) acetate. The enone (5) can be transformed into the keto-alcohol (7), which is an optically active substance, enantiomer or racemic body, by first being changed into the epoxy form (6) by means of the reaction with peroxides such as t-butylhydroperoxide and m-chloroperoxybenzoic acid, and then by being reduced with, for example, diphenyldiselenide under the presence of thiols (J. Org. Chem. 59, 5179–5183 (1994)).

Here, amines such as triethylamine and diisopropylethylamine, amide bases such as lithium diisopropylamide and potassium bis(trimethylsilyl)amide, and inorganic bases such as sodium hydride can be used as the bases. Silane compounds such as trimethylsilyl chloride, trimethylsilyl iodide and t-butyldimethylsilyl chloride can be used as the silylation agents. As reaction solvents, inert solvents such as benzene, toluene, tetrahydrofuran and acetonitrile can be cited.

The keto-alcohol (7), which is an optically active substance, enantiomer or racemic body, can be transformed into the compound (9) by changing it into the ketone form (8), which is an optically active substance, enantiomer or racemic body, directly or if necessary after protecting a hydroxyl group of the keto-alcohol (7) with a common protective group for a hydroxyl group, followed by reacting it with, for example, alcohol or thiol under the presence of Lewis acids such as boron trifluoride-diethylether complex. The keto-alcohol (7) and its hydroxyl group-protected type are together represented by the formula (8). Then, it is possible to change it to the ketal or thioketal (9), which is an optionally active substance, enantiomer or racemic body, with $Z^2$ that is a hydrogen atom, by deprotecting if $Z^2$ is the common protective group for the hydroxyl group. The ketal or thioketal (9) with $Z^2$ of a hydrogen atom can be transformed into the compound (10), which is an optically active substance, enantiomer or racemic body, by oxidation of the hydroxyl group.

The methods described in "Protective Groups in Organic Synthesis", Theodora W. G Reene and Peter G. M. Wuts can be employed for the protection and deprotection of the hydroxyl group, and ketalation and thioketalation of the carbonyl group herein. Oxidation means to oxidize with, for example, chromium type oxidants typified by Jones and Collins oxidations; manganese type oxidants such as potassium permanganate and manganese dioxide; dimethylsulfoxide type oxidants using, as an activater, oxalyl chloride, acetic acid anhydride, phosphorus pentoxide, sulfur trioxide-pyridine, dicyclohexylcarbodiimide (DCC), etc; cerium type oxidants such as cerium diammonium nitrate and cerium sulfate; ruthenium type oxidants such as tetrapropylammonium perrutheniumate and ruthenium oxide; and a Dess-Martin agent (see "Oxidations in Organic Chemistry", American Chemical Society, Washington, D.C., 1990, Milos Hudlicky): or to oxidize with oxygen under the presence of a catalyst such as palladium and platinum. For example, it can be performed in inert solvents such as ethers such as tetrahydrofran and diethylether, hydrocarbons such as toluene and benzene, halogen type solvents such as dichloromethane and chloroform, ketone type solvents such as acetone and ethylmethylketone, acetonitrile, N,N-dimethylformamide, acetic acid, pyridine, water and mixtures thereof.

The racemic body (5), (6), (7), (8), (9) or (10) can be directly optically resolved by use of the HPLC method employing chiral carriers such as cellulose carbamate derivatives and amylose carbamate derivatives. They can also be optically resolved by being changed into salts with optically active amines such as (+) or (−)-1-phenylethylamine, (+) or (−)-2-amino-1-butanol, (+) or (−)-alaninol, brucine, cinchonidine, cinchonine, quinine, quinidine and dehydroabiethylamine, after an ester moiety of the racemic body (5), (6), (7), (8), (9) or (10) is transformed into a carboxylic acid by hydrolysis under normal basic or acidic ester hydrolysis conditions. Further, they can be resolved after being changed into amido forms by use of primary or secondary optically active amines such as (+) or (−)-1-phenylethylamine, (+) or (−)-2-amino-1-butanol and (+) or (−)-alaninol, and normal amidation agents such as dicyclohexylcarbodiimide (DCC).

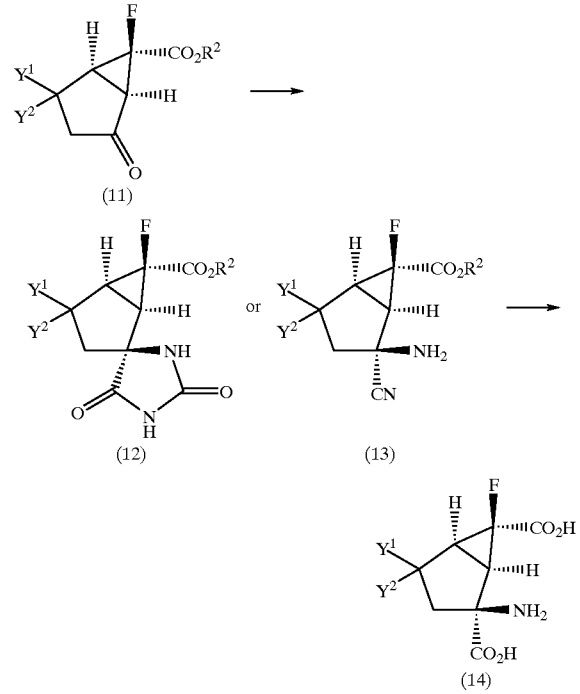

The ketones (11) including the compounds (3), (7) and (10) are useful as intermediates to synthesize the compounds according to the present invention. The ketones (11), which are optically active substances, enantiomers or racemic bodies, can be made into hydantoin derivatives (12) or amino cyanide derivatives (13) by Strecker Amino Acid Synthesis (Ann., 75, 27 (1850); 91, 349 (1850)), the Bucherer-Bergs Reaction (J. Prakt. Chem., 140, 69 (1934)), or a variation of these. The hydantoin derivatives (12) and the amino cyanide derivatives (13) can be made into the compounds of the present invention, which are optically active substances, enantiomers or racemic bodies, 4-substituted-2-amino-6-fluorobicyclo[3.1.0]hexane-2,6-dicarboxylic acids (14), by basic hydrolysis with, for example, sodium hydroxide, barium hydroxide, etc.

For instance, in the case wherein $Y^1$ and $Y^2$ in the hydantoin derivatives (12) or the amino cyanide derivatives (13) together represent —S(CH$_2$)$_n$S—, or identically or differently represent a $C_{1-10}$ alkylthio group, a $C_{3-8}$ cycloalkylthio group or a $C_{3-8}$ cycloalkyl-$C_{1-5}$ alkylthio group, one of the compounds (14) according to the present invention, 2-amino-6-fluoro-4,4-dialkylthiobicyclo[3.1.0]hexane-2,6-dicarboxylic acid, which is an optically active substance, enantiomer or racemic body, can be made by conducting basic hydrolysis for the compounds (12) or (13) with sodium hydroxide, barium hydroxide, etc. On the other hand, the hydantoin derivatives (12) and the amino cyanide derivatives (13) can be made into one of the compounds (14) according to the present invention, 2-amino-6-fluoro-4-oxobicyclo[3.1.0]hexane-2,6-dicarboxylic acid, which is an optically active substance, enantiomer or racemic body, by hydrolysis under acidic conditions using, for example, sulfuric acid or the like. Incidentally, 2-amino-6-fluoro-4-oxobicyclo[3.1.0]hexane-2,6-dicarboxylic acid, which is an optically active substance, enantiomer or racemic body, can also be obtained by removal of a dialkylthio group from 2-amino-6-fluoro-4,4-dialkylthiobicyclo[3.1.0]hexane-2,6-dicarboxylic acid, which is an optically active substance, enantiomer or racemic body (see "Protective Groups in organic Synthesis", Theodora W. Greene and Peter G. M. Wuts). Further, 2-amino-6-fluoro-4-oxobicyclo[3.1.0]hexane-2,6-dicarboxylic acid, which is an optically active substance, enantiomer or racemic body, can also be obtained by, for example, oxidation of a hydroxyl group of 2-amino-6-fluoro-4-hydroxybicyclo[3.1.0]hexane-2,6-dicarboxylic acid, which is an optically active substance, enantiomer or racemic body, (see "Oxidations in Organic Chemistry", American Chemical Society, Washington, D.C., 1990, Milos Hudlicky). During this, it is preferable to protect the carboxyl and amino groups of the compounds (14), if necessary (see, "Protecting Groups in Organic Synthesis", Theodora W. Greene, John Wilely & Sons Inc.).

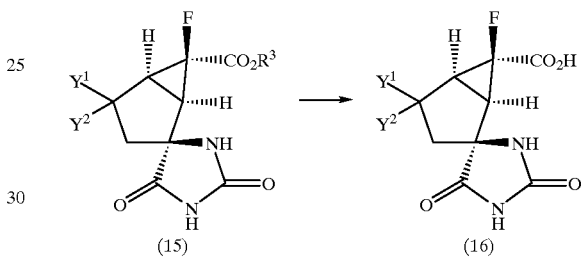

The racemic body of the formula (15) can be directly optically resolved by use of the HPLC method employing chiral carriers such as cellulose carbamate derivatives and amylose carbamate derivatives. The racemic body (15) can also be optically resolved by being changed into salts with optically active amines such as (+) or (−)-1-phenylethylamine, (+) or (−)-2-amino-1-butanol, (+) or (−)-alaninol, brucine, cinchonidine, cinchonine, quinine, quinidine and dehydroabiethylamine, after an ester moiety of the racemic body (15) is hydrolyzed to form a carboxylic acid (16) by hydrolysis under normal basic or acidic ester hydrolysis conditions. Further, it can be resolved after being changed into an amido form by use of primary or secondary optically active amines such as (+) or (−)-1-phenylethylamine, (+) or (−)-2-amino-1-butanol and (+) or (−)-alaninol, and normal amidation agents such as dicyclohexylcarbodiimide (DCC).

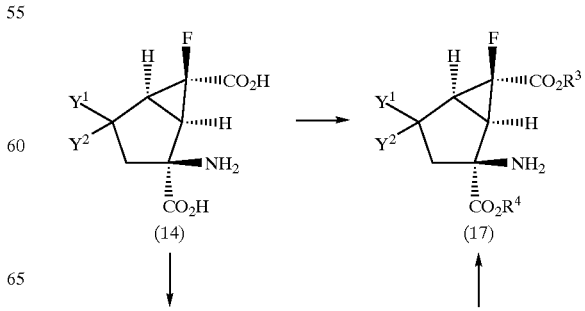

-continued

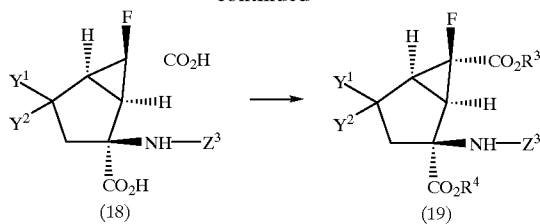

As shown in the above reaction formula, the 4-substituted-2-amino-6-fluorobicyclo[3.1.0]hexane-2,6-dicarboxylic acid (14), which is the compound according to the present invention and is present as an optically active substance, enantiomer or racemic body, can be transformed into the compound according to the present invention represented by the formula (17), the ester form of the 4-substituted-2-amino-6-fluorobicyclo[3.1.0]hexane-2,6-dicarboxylic acid, which is present as an optically active substance, enantiomer or racemic body, by esterification with common methods using alcohols represented by $R^3$—OH or $R_4$—OH; or by transformation into the compound represented by the formula (19) by esterification with common methods using alkylhalides represented by $R^3$—X' or $R^4$—X' or alcohols represented by $R^3$—OH or $R^4$—OH after changing it into the compound (18) by protecting an amino group with a protecting group represented by $Z^3$, followed by deprotecting of the protecting group $Z^3$ for the amino group.

Protection, esterification and deprotection of an amino group in the above, can be performed in accordance with normal methods ("Protective Groups in organic Synthesis", Theodora W. Greene and Peter G. M. Wuts).

If the compound (17) is a racemic body, it can be optically resolved by a general optical resolution using an acidic chiral resolving agent. If the compound (18) is a racemic body, it can be optically resolved by a general optical resolution using a basic chiral resolving agent.

Here, as the acidic chiral resolving agent, one can use optically active organic acids such as (+) or (−)-di-p-toluoyl tartaric acid, (+) or (−)-dibenzoyl tartaric acid, (+) or (−)-tartaric acid, (+) or (−)-mandelic acid, (+) or (−)-camphoric acid, and (+) or (−)-camphorsulfonic acid. As the basic chiral resolving agent, one can use, for example, optically active amines such as (+) or (−)-1-phenylethylamine, (+) or (−)-2-amino-1-butanol, (+) or (−)-alaninol, brucine, cinchonidine, cinchonine, quinine, quinidine, dehydroabiethylamine, etc.

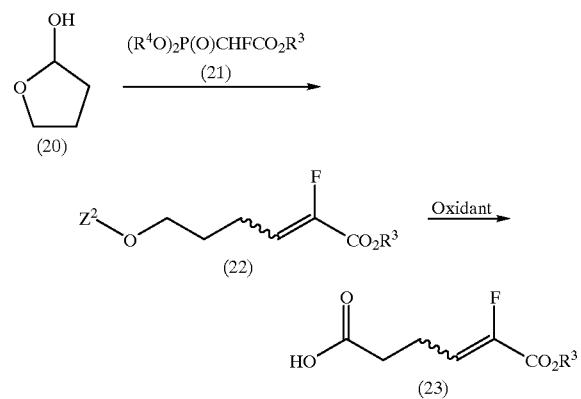

As shown in the above reaction formula, the Z form (1) and E form (2) of the fluoroacrylic acid derivative or a mixture of the Z and E forms represented by the formula (23) can be obtained by making the compound (22) by the reaction of γ-butyrolactol (20) with the phosphonoacetic acid derivative (21), followed by oxidation of a hydroxyl group to a carboxylic acid directly or after protecting the hydroxyl group.

The protection of the hydroxyl group can be performed in accordance with normal protecting methods for a hydroxyl group ("Protective Groups in Organic Synthesis", Theodora W. G Reene and Peter G. M. Wuts). As the specific embodiments of the oxidation, one can cite, for example, direct oxidation to a carboxylic acid by use of chromium type oxidants such as Jones reagent, pyridinium dichromate (PDC) or manganese type oxidants such as potassium permanganate; or stepwise oxidation to a carboxylic acid by, for example, sodium chlorite, etc. after changing it into an aldehyde by oxidation with, for example, dimethylsulfoxide such as Swern oxidation ("Oxidations in Organic Chemistry", American Chemical Society, Washington D.C., 1990, Milos Hudlicky).

The compounds (22) wherein $Z^2$ is a t-butyldimethylsilyl group, a t-butyldiphenylsilyl group, or the like, can be divided into two isomers of the Z and E forms by use of silicagel column chromatography, etc.

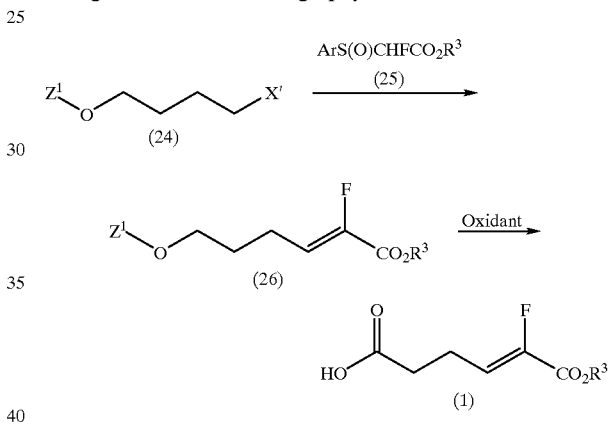

Further, as shown in the above reaction formula, the Z form (1) of the fluoroacrylic acid derivative can be obtained by oxidation with or without deprotecting the protecting group $Z^1$ of a hydroxyl group, after preparation of the compound (26) by reaction of the halide represented by the formula (24) and the sulfoxide derivative (25).

The deprotection of the protecting group $Z^1$ can be performed in accordance with normal methods (see "Protective Groups in Organic Synthesis", Theodora W. G Reene and Peter G. M. Wuts). As the specific embodiments of the oxidation, one can cite, for example, direct oxidation to carboxylic acid by use of chromium type oxidants such as Jones reagent, pyridinium dichromate (PDC) or manganese type oxidants such as potassium permanganate; or stepwise oxidation to a carboxylic acid by, for example, sodium chlorite, etc. after changing it to an aldehyde by oxidation with, for example, dimethylsulfoxide such as Swern Oxidation.

The compounds according to the present invention can be made into pharmaceutical preparations by combining with one or more pharmaceutically acceptable carriers, excipients, or diluents. Examples of said carriers, excipients and diluents include water, lactose, dextrose, fructose, sucrose, sorbitol, mannitol, polyethylene glycol, propylene glycol, starch, gum, gelatin, arginate, calcium silicate, calcium phosphate, cellulose, water syrup, methyl cellulose, polyvinyl pyrrolidone, alkyl parahydroxy benzoate, talc, magnesium stearate, stearic acid, glycerin, and oils such as sesame oil, olive oil and soybean oil.

The compounds according to the present invention, after being mixed with these carriers, excipients or diluents, and, if necessary, with additives such as generally used fillers, binders, disintegrants, pH regulators and solubilizers, can, by means of usual formulation technology, be prepared as pharmaceutical preparations for oral or parenteral administration, especially as preparations that act on group 2 metabotropic glutamate receptors (group 2 metabotropic glutamate receptor agonists) and that prevent or treat psychiatric or neurological diseases, in such forms as tablets, pills, capsules, granules, powders, liquids, emulsions, suspensions, ointments, injections and skin plasters. The compounds according to this invention can be administered orally or parenterally to an adult patient in a quantity of 0.01–500 mg in a single or in divided doses per day. This dosage can be increased or decreased as appropriate in consideration of the type of disease being treated and the patient's age, weight and symptoms.

BEST MODE FOR CARRYING OUT THE INVENTION

In the following, we describe this invention specifically by presenting working examples and experimental examples. However, this invention is not thereby limited to these examples.

EXAMPLE 1

Synthesis of (1RS, 5RS, 6RS)ethyl 6-fluoro-2-oxobicyclo[3.1.0]hexane-6-carboxylate (1) Under a nitrogen flow, with ice-cooling, 78.0 ml of a 1.00M tetrahydrofuran solution of sodium bis(trimethylsilyl)amide was added dropwise over 40 min to a solution of 18.9 g of ethyl diethylphosphonofluoroacetate in 75 ml of tetrahydrofuran, and then the mixture was further stirred for 45 min. A pre-prepared solution of γ-butyrolactol (at −78° C., under a nitrogen flow, 70.3 ml of a 1.01 M toluene solution of aluminum diisobutylhydride was added dropwise over 1.5 hours to 6.1 g of γ-butyrolactone in 75 ml of tetrahydrofuran, and then the mixture was further stirred at this temperature for more 1.5 hours) was added dropwise over 30 min to this reaction solution. The ice-bath was taken off after the addition. The reaction solution was quenched with 120 ml of 6N hydrochloric acid after stirring it for 2 hours at room temperature, and then 3 hours at 30° C. The reaction solution was extracted twice with ethyl acetate. The obtained organic layers were consolidated, and dried over anhydrous sodium sulfate after being washed with a saturated aqueous solution of sodium chloride. After filtering off the desiccant, concentration of the filtrate was carried out under reduced pressure. The residue was purified by column chromatography (silica gel: Wako gel C200 (made by Wako Pure Chemical Industries Ltd.,) eluent: hexane-ethyl acetate=4:1 to 2:1), yielding 7.9 g of a mixture of the Z and E forms with the ratio of about 1:3 of ethyl 2-fluoro-6-hydroxy-2-hexenoate.

The proton NMR data of the obtained compounds are shown below. $^1$H-NMR(CDCl$_3$)δ(ppm); 1.34(3H*1/4, t, J=7.1 Hz), 1.36(3H*3/4, t, J=7.1 Hz), 1.73(2H, quint., J=6.6 Hz), 2.01(1H, br.s), 2.30–2.41(2H*1/4, m), 2.56–2.68 (2H*3/4, m), 3.63–3.73(2H*, m), 4.30(2H*1/4, q, J=7.1 Hz), 4.32(2H*3/4, q, J=7.1 Hz), 5.94(1H*3/4, dt, J=21.3, 8.7 Hz), 6.16(1H*1/4, dt, J=33.2, 8.1 Hz)

(2) 7.8 g of the mixture of the Z and E forms with the ratio of about 1:3 of ethyl 2-fluoro-6-hydroxy-2-hexenoate, and 14.6 g of t-butyldiphenylchlorosilane were dissolved into 40 ml of N,N-dimethylformamide, and then 4.5 g of imidazole was added with ice-cooling. The reaction solution was warmed up to room temperature, and then diluted with ethyl acetate. After washing the organic layer with water, a saturated aqueous solution of ammonium chloride, a saturated aqueous solution of sodium hydrogen carbonate and a saturated aqueous solution of sodium chloride, in sequence, it was dried over anhydrous sodium sulfate. After filtering off the desiccant, concentration of the filtrate was carried out under reduced pressure. The residue was separated into each geometrical isomer and purified by column chromatography (silica gel: MSG D-40-60A (made by Dokai Chemicals Ltd.), eluent: hexane-ethyl acetate=50:1), yielding 2.4 g of ethyl 2-fluoro-6-t-butyldiphenylsilyloxy-2(Z)-hexenoate and 7.1 g of ethyl 2-fluoro-6-t-butyldiphenylsilyloxy-2(E)-hexenoate.

The proton NMR and mass spectrograph date of ethyl 2-fluoro-6-t-butyldiphenylsilyloxy-2(Z)-hexenoate are shown below.

$^1$H-NMR(CDCl$_3$)δ(ppm); 1.05(9H, s), 1.33(3H, t, J=7.1 Hz), 1.61–1.76(2H, m), 2.31–2.43(2H, m), 3.68(2H, t, J=6.2 Hz), 4.27(2H, q, J=7.1 Hz), 6.14(1H, dt, J=33.4, 7.8 Hz), 7.33–7.48(6H, m), 7.62–7.70(4H, m) MS(Cl) (Pos)m/e; 415(M$^+$+1), 357(M$^+$−57), 337(M$^+$−77, 100%)

The proton NMR and mass spectrograph data of ethyl 2-fluoro-6-t-butyldiphenylsilyloxy-2(E)-hexenoate are shown below.

$^1$H-NMR(CDCl$_3$)δ(ppm); 1.05(9H, s), 1.32(3H, t, J=7.1 Hz), 1.61–1.77(2H, m), 2.56–2.69(2H, m), 3.69(2H, t, J=6.3 Hz), 4.28(2H, q, J=7.1 Hz), 5.92(1H, dt, J=21.8, 8.1 Hz), 7.33–7.48(6H, m), 7.62–7.70(4H, m) MS(Cl) (Pos)m/e; 415(M$^+$+1), 357(M$^+$−57), 337(M$^+$−77, 100%)

(3) 2.3 g of ethyl 2-fluoro-6-t-butyldiphenylsilyloxy-2 (Z)-hexenoate was dissolved into 12 ml of acetone, and then 9 ml of 8N Jones agent was added with ice-cooling. After stirring the reaction solution at room temperature for 2.5 hours, the excessive agent was quenched by adding 2-propanol to the reaction solution with ice-cooling. The reaction mixture was diluted with ethyl acetate, and then washed with water. The aqueous layer was extracted with ethyl acetate, and the organic layer was washed in total with water twice and with a saturated aqueous solution of sodium chloride, and then it was dried over anhydrous sodium sulfate. After filtering off the desiccant, concentration of the filtrate was carried out under reduced pressure. The residue was purified by column chromatography (silica gel: Wako gel C200 (made by Wako Chemical Industries Ltd.), eluent: hexane-ethyl acetate=3:1), yielding 970 mg of ethyl 2-fluoro-5-carboxy-2(Z)-pentenoate.

The proton NMR and mass spectrograh data are shown below. $^1$H-NMR(CDCl$_3$)δ(ppm); 1.34(3H, t, J=7.1 Hz), 2.46–2.60(4H, m), 4.29(2H, q, J=7.1 Hz), 6.03–6.27(1H, m) MS(Cl) (Pos)m/e; 191(M$^+$+1, 100%)

Likewise, ethyl 2-fluoro-5-carboxy-2(E)-pentenoate was obtained. The proton NMR and mass spectrograph data are shown below. $^1$H-NMR(CDCl$_3$)δ(ppm); 1.36(3H, t, J=7.1 Hz), 2.54(2H, t, J=7.3 Hz), 2.78–2.90(2H, m), 4.32(2H, q, J=7.1 Hz), 5.98(1H, dt, J=20.5, 8.2 Hz) MS(Cl) (Pos)m/e; 191(M$^+$+1), 173(M$^+$−17, 100%)

(4) 920 mg of ethyl 2-fluoro-5-carboxy-2(Z)-pentenoate and 1.3 ml of oxalylchloride in hexane were heated under reflux for 3 hours. The reaction solution was concentrated under reduced pressure, and dried by use of a vacuum pump.

An ether solution of an excess of diazomethane was added dropwise to the obtained residue with ice-cooling, this was stirred at room temperature for 1 hour. After filtering the reaction solution, the filtrate was concentrated under reduced pressure. The obtained residue was dissolved into 10 ml of benzene, and this was added dropwise over 30 min to 120 ml of benzene solution of 40 mg of copper (II) bis(N-t-butylsalicylaldiimidate), under heat-refluxing. The reaction solution was cooled down to room temperature, and concentrated under reduced pressure. The residue was purified by column chromatography (silica gel: Wako gel C200 (made by Wako Chemical Industries Ltd.), eluent: hexane-acetone=9:1), yielding 263 mg of (1RS,5RS,6RS)ethyl 6-fluoro-2-oxobicyclo[3.1.0]hexane-6-carboxylate.

The proton NMR and mass spectrograph data are shown below.

$^1$H-NMR(CDCL$_3$)δ(ppm); 1.33(3H, t, J=7.1 Hz), 2.05–2.55(4H, m), 2.59(1H, d, J=6.6 Hz), 2.70–2.77(1H, m), 4.30(2H, q, J=7.1 Hz) MS(IonSpray) (Pos)m/e; 187(M$^+$+1), 204(M$^+$+18), 209(M$^+$+23, 100%)

Likewise, (1RS,5RS,6SR)ethyl 6-fluoro-2-oxobicyclo[3.1.0]hexane-6-carboxylate was obtained. The proton NMR and mass spectrograph are shown below.

$^1$H-NMR(CDCL$_3$)δ(ppm); 1.36(3H, t, J=7.1 Hz), 2.00–2.80(6H, m), 4.32(2H, q, J=7.1 Hz)

MS(IonSpray) (Pos)m/e; 187(M$^+$+1, 100%)

EXAMPLE 2

Synthesis of (1RS,5RS,6RS)ethyl 6-fluoro-2-oxobicyclo[3.1.0]hexane-6-carboxylate (1) 3.7 g of 60% sodium hydride (oily) was suspended in 85 ml of N,N-dimethylformamide, and then 19.6 g of ethyl phenylsulfinylfluoroacetate in 35 ml of N,N-dimethylformamide was added dropwise over 30 min thereto with ice-cooling. After the addition, stirring was continued for 30 min with ice-cooling, and then further stirring was continued for 30 min at room temperature. With ice-cooling, 20.2 g of 1-bromo-4-tetrahydropyranyloxybutane was added at a time thereto, and then stirring was continued at roompemperature for 4 hours and at 95–110° C. for 1 hour. After cooling the reaction solution down to room temperature, it was poured into ice water and was extracted with 10% hexane-ethyl acetate. The obtained organic layer was dried over anhydrous sodium sulfate after being washed with water and a saturated aqueous solution of sodium chloride. After filtering off the desiccant, concentration of the filtrate was carried out under reduced pressure. The residue was purified by column chromatography ((silica gel: Wako gel C200 (made by Wako Pure Chemical Industries Ltd.), eluent: hexane-ethyl acetate=15:1) and (silica gel: MSG D-40-60A (made by Dokai Chemicals Ltd.), eluent: hexane-acetone=20:1), yielding 7.4 g of ethyl 2-fluoro-6-tetrahydropyranyloxy-2(Z)-hexenoate.

The proton NMR and mass spectrograph data are shown below.

$^1$H-NMR(CDCL$_3$)δ(ppm); 1.33(3H, t, J=7.1 Hz), 1.46–1.90(8H, m), 2.30–2.41(2H, m), 3.33–3.57(2H, m), 3.72–3.90(2H, m), 4.28(2H, q, J=7.1 Hz), 4.57–4.60(1H, m), 6.17(1H, dt, J=33.3, 7.8 Hz) MS(CI) (Pos)m/e; 261(M$^+$+1), 85(M$^+$−175, 100%)

(2) 4.7 g of ethyl 2-fluoro-5-carboxy-2(Z)-pentenoate was obtained according to step (3) of Example 1.

The proton NMR and mass spectrograph data are shown below.

$^1$H-NMR(CDCL$_3$)δ(ppm); 1.34(3H, t, J=7.1 Hz), 2.46–2.60(4H, m), 4.29(2H, q, J=7.1 Hz), 6.03–6.27(1H, m)

MS(CI) (Pos)m/e; 191(M$^+$+1, 100%)

(3) 2.8 g of (1RS,5RS,6RS)ethyl 6-fluoro-2-oxobicyclo[3.1.0]hexane-6-carboxylate was obtained according to step (4) of Example 1.

The proton NMR and mass spectrograph data are shown below.

$^1$H-NMR(CDCL$_3$)δ(ppm); 1.33(3H, t, J=7.1 Hz), 2.05–2.55(4H, m), 2.59(1H, d, J=6.6 Hz), 2.70–2.77(1H, m), 4.30(2H, q, J=7.1 Hz)

MS(IonSpray) (Pos)/m/e; 187(M$^+$+1), 204(M$^+$+18), 209(M$^+$+23, 100%)

EXAMPLE 3

Synthesis of (1R*,5R*,6R*)ethyl 6-fluoro-2-oxobicyclo[3.1.0]hexane-6-carboxylate 919 mg of (1RS,5RS,6RS)ethyl 6-fluoro-2-oxobicyclo[3.1.0]hexane-6-carboxylate which was obtained according to step (4) of Example 1 was resolved by use of the HPLC with CHIRALPAK AD (made by Diacel Chemicals Industries Ltd., 2.0*25 cm, eluent: n-hexane/2-propanol=3:1, Flow Rate: 5.0 ml/min, Temp.: room temp., Detect: UV210 nm), yielding 423 mg of (+)-(1R*,5R*,6R*)ethyl 6-fluoro-2-oxobicyclo[3.1.0]hexane-6-carboxylate and 405 mg of (−)-(1R*,5R*,6R*)ethyl 6-fluoro-2-oxobicyclo[3.1.0]hexane-6-carboxylate.

(+)-(1R*,5R*,6R*)ethyl 6-fluoro-2-oxobicyclo[3.1.0]hexane-6-carboxylate $^1$H-NMR(CDCL$_3$)δ(ppm): 1.33(3H, t, J=7.1 Hz), 2.05–2.55(4H, m), 2.59(1H, d, J=6.6 Hz), 2.70–2.77(1H, m), 4.30(2H, q, J=7.1 Hz)

MS(IonSpray) (Pos)m/e: 187(M$^+$+1), 204(M$^+$+18), 209(M$^+$+23, 100%) T$_R$=5.65 min (CHIRALPAK AD 0.46*25 cm, Eluent: n-Hexane/2-propanol=3:1, Flow rate: 1.0 mL/min, Temp.; rt., Detect: UV210 nm)

[α]$_D^{27}$=+27.98(c=0.13, CHCL$_3$)

(−)-(1R*,5R*,6R*)ethyl 6-fluoro-2-oxobicyclo[3.1.0]hexane-6-carboxylate $^1$H-NMR(CDCL$_3$)δ(ppm); 1.33(3H, t, J=7.1 Hz), 2.05–2.55(4H, m), 2.59(1H, d, J=6.6 Hz), 2.70–2.77(1H, m), 4.30(2H, q, J=7.1 Hz)

MS(IonSpray) (Pos)m/e: 187(M$^+$+1), 204(M$^+$+18), 209(M$^+$+23, 100%) T$_R$=9.13 min (CHIRALPAK AD 0.46*25 cm, Eluent: n-Hexane/2-propanol=3:1, Flow rate: 1.0 mL/min, Temp.; rt., Detect: UV210nm)

[α]$_D^{27}$=−30.33(c=0.16, CHCL$_3$)

EXAMPLE 4

Synthesis of (1RS,2SR,5RS,6RS)-2-spiro-5'-hydantoin-6-fluorobicyclo[3.1.0]hexane-6-carboxylic acid 256 mg of (1RS,5RS,6RS)ethyl 6-fluoro-2-oxobicyclo[3.1.0]hexane-6-carboxylate was dissolved into 2.5 ml of ethanol. 1.4 ml of 1N aqueous solution of sodium hydroxide was added dropwise thereto with ice-coolinyg, and then, stirring was continued at this temperature for 10 min. After acidifying the reaction solution with 1N hydrochloric acid (pH was nearly equal to 1), it was diluted with ethyl acetate, and washed with a saturated aqueous solution of sodium chloride. The aqueous layer was extrated twice with ethyl acetate, and the obtained organic layers were consolidated to be dried over anhydrous sodium sulfate. After filtering off the desiccant, concentration of the filtrate was carried out under reduced pressure. The residue obtained was dissolved into 2 ml of a mixture of water and ethanol (1:1), and it was stirred at 55° C. for 8.5 hours after 796 mg of ammonium carbonate and 277 mg of potassium cyanide were added thereto. The reaction mixture was ice-cooled, and then it was neutralized by adding concentrated hydrochloric acid. It was purified by ion exchange chromatography (AG50W-X8 cation exchange resin (Bio-Rad), eluent: water), yielding 320 mg of (1RS,2SR,5RS,6RS)-2-spiro-5'-hydantoin-6-fluorobicyclo[3.1.0]hexane-6-carboxylic acid. The proton NMR and mass spectrograph data are shown below.

$^1$H-NMR(DMSO-d$_6$)δ(ppm); 1.49–1.70(1H, m), 1.93–2.40(5H, m), 8.08(1H, s), 10.71(1H, s)

MS(CI) (Pos)m/e; 229(M$^+$+1, 100%)

Likewise, the following compounds were obtained. Physical property data for each are shown together. (1RS,2SR,5RS,6SR)-2-spiro-5'-hydantoin-6-fluorobicyclo[3.1.0]hexane-6-carboxylic acid.

$^1$H-NMR(DMSO-d$_6$)δ(ppm); 1.80–2.38(6H, m), 7.34(1H, s), 10.74(1H, s)

MS(CI) (Pos)m/e; 229(M$^+$+1, 100%)

(+)-(1R*,2S*,5R*,6R*)-2-spiro-5'-hydantoin-6-fluorobicyclo[3.1.0]hexane-6-carboxylic acid.

$^1$H-NMR(DMSO-d$_6$)δ(ppm); 1.49–1.70(1H, m), 1.93–2.40(5H, m), 8.08(1H, s), 10.71(1H, s)

MS(CI) (Pos)m/e; 229(M$^+$+1, 100%)

$[α]_D^{25.5}$=+77.87(c=0.43, 1N NaOH)

(−)-(1R*,2S*,5R*,6R*)-2-spiro-5'-hydantoin-6-fluorobicyclo[3.1.0]hexane-6-carboxylic acid.

$^1$H-NMR(DMSO-d$_6$)δ(ppm); 1.49–1.70(1H, m), 1.93–2.40(5H, m), 8.08(1H, s), 10.71(1H, s)

MS(CI) (Pos)m/e; 229(M$^+$+1, 100%)

$[α]_D^{25.5}$=−77.30(c=0.41, 1N NaOH)

EXAMPLE 5

Synthesis of (1RS,2SR,5RS,6RS)-2-amino-6-fluorobicyclo[3.1.0]hexane-2,6-dicarboxylic acid 200 mg of (1RS,2SR,5RS,6RS)-2-spiro-5'-hydantoin-6-fluorobicyclo[3.1.0]hexane-6-carboxylic acid was stirred in 3.0 ml of 60% sulfuric acid at 140° C. for 6 days. After ice-cooling and neutralizing the reaction solution with 5N aqueous solution of sodium hydroxide, it was purified by ion exchange chromatography (AG50W-X8 cation exchange resin (Bio-Rad), eluent: water-50% THF/water-10% pyridine/water), yielding 61 mg of (1RS,2SR,5RS,6RS)-2-amino-6-fluorobicyclo[3.1.0]hexane-2,6-dicarboxylic acid. The proton NMR and mass spectrograph data are shown below.

$^1$H-NMR(TFA-d)δ(ppm); 2.15–2.28(1H, m), 2.57(1H, dd, J=13.5, 8.6 Hz), 2.67–2.94(4H, m)

MS(IonSpray) (Nega)m/e; 202(M$^+$−1, 100%)

Likewise, the following compounds were obtained. Physical properties data for each are shown together. (1RS,2SR,5RS,6SR)-2-amino-6-fluorobicyclo[3.1.0]hexane-2,6-dicarboxylic acid.

$^1$H-NMR(TFA-d)δ(ppm); 2.36–2.54(2H, m), 2.58–2.87(4H, m)

MS(CI) (IonSpray) (Nega)m/e; 202(M$^+$−1, 100%)

(−)-(1R*,2S*,5R*,6R*)-2-amino-6-fluorobicyclo[3.1.0]hexane-2,6-dicarboxylic acid.

$^1$H-NMR(TFA-d)δ(ppm); 2.15–2.28(1H, m), 2.57(1H, dd, J=13.5, 8.6 Hz), 2.67–2.94(4H, m)

MS(IonSpray) (Nega)m/e; 202(M$^+$−1, 100%)

$[α]_D^{26}$=−58.81(c=0.14, H$_2$O)

(+)-(1R*,2S*,5R*,6R*)-2-amino-6-fluorobicyclo[3.1.0]hexane-2,6-dicarboxylic acid.

$^1$H-NMR(TFA-d)δ(ppm); 2.15–2.28(1H, m), 2.57(1H, dd, J=13.5, 8.6 Hz), 2.67–2.94(4H, m)

MS(IonSpray) (Nega)m/e; 202(M$^+$−1, 100%)

$[α]_D^{26}$=+57.49(c=0.16, H$_2$O)

EXAMPLE 6

Synthesis of (1RS,5RS,6RS)ethyl 6-fluoro-2-oxobicyclo[3.1.0]hex-3-en-6-carboxylate Under a nitrogen atmosphere, 19.5 g of (1RS,5RS,6RS)ethyl 6-fluoro-2-oxobicyclo[3.1.0]hexane-6-carboxylate dissolved into 230 ml of tetrahydrofuran at −78° C. was added dropwise to 230 ml of a tetrahydrofuran solution of lithium bis(trimethylsilyl)amide which was prepared from 78 ml of n-butyllithium (1.61M hexane solution) and 20.3 g of 1,1,1,3,3,3-hexamethyldisilazane. After stirring at this temperature for 1 hour, 19.8 ml of chlorotrimethylsilane was added thereto, and this was stirred at room temperature for 1.5 hours. After carrying out of concentration of the reaction solution under reduced pressure, anhydrous hexane was added to the residue, the resulting inorganic salt was filtered off, and the filtrate was further concentrated under reduced pressure. After the residue was dissolved into 240 ml of acetonitrile, 25.9 g of palladium acetate was added thereto, and then it was stirred at room temperature for one day. The reaction solution was diluted with 240 ml of diethyl ether, the palladium was filtered off by use of celite, and the filtrate was concentrated under reduced pressure. The residue was purified by column chromatography (silica gel: Wako gel C200 (made by Wako Pure Chemical Industries Ltd.), eluent: hexane-ethyl acetate=9:1 to 5:1), yielding 17.1 g of (1RS,5RS,6RS)ethyl 6-fluoro-2-oxobicyclo[3.1.0]hex-3-en-6-carboxylate.

The proton NMR and mass spectrograph data are shown below.

$^1$H-NMR(CDCL$_3$)δ(ppm); 1.34(3H, t, J=7.3 Hz), 2.78(1H, dt, J=0.6, 5.8 Hz), 3.22(1H, dd, J=2.9, 5.8 Hz), 4.31(2H, q, J=7.3 Hz), 6.07(1H, dd, J=0.6, 5.6 Hz), 7.42(1H, ddd, J=0.6, 2.9, 5.6 Hz)

MS(CI) (Pos)m/e; 185(M$^+$+1, 100%)

EXAMPLE 7

Synthesis of (1RS,3RS,4RS,5SR,6RS)ethyl 3,4-epoxy-6-fluoro-2-oxobicyclo[3.1.0]hexane-6-carboxylate 16.9 g of (1RS,5RS,6RS)ethyl 6-fluoro-2-oxobicyclo[3.1.0]hex-3-ene-6-carboxylate was dissolved into 100 ml of toluene. 30.6 ml of 70% t-butylhydroxyperoxide aqueous solution and 11.5 ml of 10% benzyltrimethylammoniumhydroxide/methanol solution were added thereto, and this was stirred at room temperature for 4 hours. After the reaction solution was poured into water, it was extracted twice with ethyl acetate. The obtained organic layers were consolidated to be washed with a saturated aqueous solution of sodium chloride, and dried over anhydrous sodium sulfate. After filtering off the desiccant, concentration of the filtrate was carried out under reduced pressure. The residue was purified by column chromatography (silica gel: Wako gel C200 (made by Wako Pure Chemical Industries Ltd.), eluent: hexane-ethyl acetate=8:1 to 6:1), yielding 13.4 g of (1RS,3RS,4RS,5SR, 6RS)ethyl 3,4-epoxy-6-fluoro-2-oxobicyclo[3.1.0]hexane-6-carboxylate. The proton NMR and mass spectrograph data are shown below.

$^1$H-NMR(CDCL$_3$)δ(ppm); 1.34(3H, t, J=7.3 Hz), 2.50 (1H, ddt, J=0.8, 2.4, 6.0 Hz), 3.19(1H, dt, J=0.8, 6.0 Hz), 3.53(1H, dt, J=0.8, 2.4 Hz), 4.02(1H, tt, J=0.8, 2.4 Hz), 4.32(2H, q, J=7.3 Hz)

MS(EI) (Pos)m/e; 99(M$^+$−101, 100%), 200(M$^+$)

EXAMPLE 8

Synthesis of (1RS,4SR,5SR,6RS)ethyl 6-fluoro-4-hydroxy-2-oxobicyclo[3.1.0]hexane-6-carboxylate Under a nitrogen atmosphere, 23.2 g of N-acetyl-L-cystein, 54.3 g of sodium tetraborate decahydrate and 0.7 g of diphenyldiselenide were suspended in 450 ml of a water-ethanol (1:1) mixture solution which had been deaerated. 9.5 g of (1RS,3RS,4RS,5SR,6RS)ethyl (3,4-epoxy-6-fluoro-2-oxobicyclo [3.1.0]hexane-6-carboxylate dissolved into 225 ml of tetrahydrofuran was added thereto, and this was stirred at room temperature for one day, at 38° C. for 12 hours, and at 85° C. for 5 hours. After the reaction solution was cooled down to room temperature, it was poured into water and extracted three times with diethyl ether. The obtained organic layers were consolidated and dried over anhydrous sodium sulfate. After filtering off the desiccant, concentration of the filtrate was carried out under reduced pressure. The residue was purified by column chromatography (silica gel: Wako gel (made by Wako Pure Chemical Industries Ltd.), eluent: hexane-ethyl acetate=3:1 to 1:1), yielding 3.9 g of (1RS,4SR,5SR,6RS)ethyl 6-fluoro-4-hydroxy-2-oxobicyclo[3.1.0]hexane-6-carboxylate. The proton NMR and mass spectrograph data are shown below.

$^1$H-NMR(CDCL$_3$)δ(ppm); 1.34(3H, t, J=7.1 Hz), 2.05 (1H, d, J=5.1 Hz), 2.30(1H, dd, J=3.5, 19.2 Hz), 2.63(1H, dt, J=5.9, 19.2 Hz), 2.72(1H, d, J=5.9 Hz), 2.85(1H, dd, J=2.1, 5.9 Hz), 4.31(2H, q, J=7.1 Hz), 4.76(1H, t, J=5.1 Hz)

MS(EI) (Pos)m/e; 129(M$^+$−73, 100%), 202(M$^+$)

EXAMPLE 9

Synthesis of (1RS,4SR,5SR,6RS)ethyl 6-fluoro-4-t-butyldimethylsilyloxy-2-oxobicyclo[3.1.0]hexane-6-carboxylate 2.8 g of (1RS,4SR,5SR,6RS)ethyl 6-fluoro-4-hydroxy-2-oxobicyclo[3.1.0]hexane-6-carboxylate and 2.5 g of t-butyldimethylchlorosilane were dissolved into 14 ml of N,N-dimethylformamide. 1.0 g of imidazole was further added thereto with ice-cooling, and this was stirred at room temperature for one day. The reaction solution was poured into water, and extracted with n-hexane-ethyl acetate (1:9). The obtained organic layer was washed with, in sequence, water and a saturated aqueous solution of sodium chloride, and then dried over anhydrous sodium sulfate. After filtering off the desiccant, concentration of the filtrate was carried out under reduced pressure. The residue was purified by column chromatography (silica gel: Wako gel (made by Wako Pure Chemical Industries Ltd.), eluent: hexane-ethyl acetate= 15:1), yielding 3.8 g of (1RS,4SR,5SR,6RS)ethyl 6-fluoro-4-t-butyldimethylsilyloxy-2-oxobicyclo[3.1.0]hexane-6-carboxylate. The proton NMR and mass spectrograph data are shown below.

$^1$H-NMR(CDCL$_3$)δ(ppm); 0.11(3H, s), 0.13(3H, s), 0.90 (9H, s) 1.33(3H, t, J=7.1 Hz), 2.21(1H, dd, J=4.0, 19.1 Hz), 2.57(1H, dt, J=5.6, 19.1 Hz), 2.60–2.72(4H, m), 4.31(2H, q, J=7.1 Hz), 4.66(1H, d, J=5.6 Hz)

MS(CI) (Pos)m/e; 259(M$^+$−57, 100%), 317(M$^+$+1)

EXAMPLE 10

Synthesis of (1RS,4RS,5RS,6SR)ethyl 2,2-ethylenedithio-6-fluoro-4-hydroxybicyclo[3.1.0]hexane-6-carboxylate 3.7 g of (1RS,4SR,5SR,6RS)ethyl 6-fluoro-4-t-butyldimethylsilyloxy-2-oxobicyclo[3.1.0]hexane-6-carboxylate and 1.2 ml of 1,2-ethanedithiol were dissolved into 37 ml of chloroform. Trifluoroborane-diethylether complex was added dropwise thereto, and this was stirred at room temperature for one day. The reaction solution was washed with, in sequence, a saturated aqueous solution of sodium hydrogen carbonate and a saturated aqueous solution of sodium chloride, and then dried over anhydrous sodium sulfate. After filtering off the desiccant, concentration of the filtrate was carried out under reduced pressure. The residue was purified by column chromatography (silica gel: Wako gel (made by Wako Pure Chemical Industries Ltd.), eluent: hexane-ethyl acetate=2:1), yielding 3.2 g of (1RS,4RS,5RS, 6SR)ethyl 2,2-ethylenedithio-6-fluoro-4-hydroxybicyclo [3.1.0]hexane-6-carboxylate. The proton NMR and mass spectrograph data are shown below.

$^1$H-NMR(CDCL$_3$)δ(ppm); 1.32(3H, t, J=7.1 Hz), 2.07 (1H, d, J=7.1 Hz), 2.38–2.69(4H, m), 3.33–3.45(4H, m), 4.27(2H, q, J=7.1 Hz), 4.50(1H, dd, J=5.5, 7.1 Hz)

MS(EI) (Pos)m/e; 131(M$^+$−147, 100%), 278(M$^+$)

EXAMPLE 11

Synthesis of (1RS,5RS,6SR)ethyl 4,4-ethylenedithio-6-fluoro-2-oxobicyclo[3.1.0]hexane-6-carboxylate 3.1 g of (1RS,4RS,5RS,6SR)ethyl 2,2-ethylenedithio-6-fluoro-4-hydroxybicyclo[3.1.0]hexane-6-carboxylate and 9.0 g of dicyclohexylcarbodiimide were dissolved into 116 ml of dimethylsulfoxide. In sequence, 1.2 ml of pyridine and 0.6 ml of trifluoroacetic acid were added dropwise thereto, and this was stirred at room temperature for one day. After filtering off the resulting urea, it was washed with ethyl acetate. The filtrate was diluted with ethyl acetate, washed with water three times and with a saturated aqueous solution of sodium chloride, and then dried over anhydrous sodium sulfate. After filtering off the desiccant, concentration of the filtrate was carried out under reduced pressure. The residue was purified by column chromatography (silica gel: Wako gel (made by Wako Pure Chemical Industries Ltd.), eluent: hexane-ethyl acetate=5:1), yielding 2.6 g of (1RS,5RS,6SR) ethyl 4,4-ethylenedithio-6-fluoro-2-oxobicyclo[3.1.0] hexane-6-carboxylate. The proton NMR and mass spectrograph data are shown below.

$^1$H-NMR(CDCL$_3$)δ(ppm); 1.35(3H, t, J=7.1 Hz), 2.79 (1H, d, J=6.3 Hz), 2.86–3.08(2H, m), 3.18(1H, dd, J=1.9, 6.3 Hz), 3.38–3.53(4H, m), 4.31(2H, q, J=7.1 Hz)

MS(EI) (Pos)m/e; 131(M$^+$−145, 100%), 276(M$^+$)

EXAMPLE 12

Synthesis of (1R*,2S*,5R*,6S*)-2-spiro-5'-hydantoin-4,4-ethylenedithio-6-fluoro-N-((R)-1-phenylethyl)bicyclo[3.1.0]hexane-6-carboxyamide (1) 1.3 g of (1RS,5RS,6SR)ethyl 4,4-ethylenedithio-6-fluoro-2-oxobicyclo[3.1.0]hexane-6-carboxylate was dissolved into 5.0 ml of ethanol. With ice-cooling, 5.0 ml of 1N aqueous solution of sodium hydroxide was added dropwise thereto, and this was stirred at this temperature for 15 min. After heating the reaction solution to room temperature, 1.1 g of ammonium carbonate and 350 mg of potassium cyanide were added thereto, and then this was stirred at 37° C. for 3 days. After ice-cooling and adjusting the pH of the reaction mixture to 1 by adding concentrated hydrochloric acid, 5 ml of ethanol was added and stirring was continued at this temperature for 1 hour. After filtering off the resulting crystals and washing with a mixture solution of ethanol-water (2:1), this was dried at 80° C., yielding 1.1 g of (1RS,2SR,5RS,6SR)-2-spiro-5'-hydantoin-4,4-ethylenedithio-6-fluorobicyclo[3.1.0]hexane-6-carboxylic acid. The proton NMR and mass spectrograph data are shown below.

$^1$H-NMR(DMSO-d$_6$)δ(ppm); 2.37–2.50(2H, m), 2.68 (1H, dd, J=1.9, 6.9 Hz), 2.76(1H, dd, J=4.2, 15.4 Hz), 3.28–3.50(4H, m), 8.10(1H, s), 10.78(1H, s)

MS(ES) (Nega)m/e; 317(M$^+$–1, 100%)

(2) 5.7 g of (1RS,2SR,5RS,6SR)-2-spiro-5'-hydantoin-4,4-ethylenedithio-6-fluorobicyclo[3.1.0]hexane-6-carboxylic acid and 2.6 g of (R)-(+)-1-phenylethylamine were dissolved into 240 ml of dimethylformamide. 3.4 g of 1-hydroxybenzotriazol monohydrate and 4.1 g of 1-ethyl-3-(3-dimethylaminopropyl)carbodiimide hydrochloride were added thereto with ice-cooling, and stirring was continued at room temperature for one day. After adding 1N hydrochloric acid to the reaction solution and extracting four times with ethyl acetate, it was dried over anhydrous sodium sulfate. After filtering off the desiccant, concentration was carried out under reduced pressure. The residue was treated by chromatography (silica gel: MSG D-40-60A (made by Dokai Chemicals Ltd.), eluent: chloroform-methanol=50:1), yielding 3.5 g of a lower polar diastereomer, (1R*, 2S*, 5R*, 6S*)-2-spiro-5'-hydantoin-4, 4-ethylenedithio-6-fluoro-N-((R)-1-phenylethyl) bicyclo [3.1.0] hexane-6-carboxyamid e (Rf value 0.74 (TLC: silica gel 60 F$_{254}$ (made by Merck), eluent: chloroform-methanol=9:1)), and 3.5 g of a polar diastereomer, (1R*, 2S*, 5R*, 6S*)-2-spiro-5'-hydantoin-4, 4-ethylenedithio-6-fluoro-N-((R)-1-phenylethyl) bicyclo [3.1.0]hexane-6carboxyamid e (Rf value 0.69 (TLC: silica gel 60 F$_{254}$ (made by Merck), eluent: chloroform-methanol= 9:1)). The melting point and specific optical rotation value of each compound are shown below.

The lower polar diastereomer m.p. 288–289° C.

[α]D$^{26=+}$62.55(c=0.21, MeOH)

The polar diastereomer m.p. 315–316° C.

[α]D$^{26=+}$52.58(c=0.24, MeOH)

EXAMPLE 13

Synthesis of (1RS, 2SR, 5SR, 6SR)-2-amino-6-fluoro-4oxobicyclo [3.1.0]hexane-2,6-dicarboxylic acid 500 mg of (1RS, 2SR, 5RS, 6SR)-2-spiro-5'-hydantoin-4,4-ethylenedithio-6-fluorobicyclo[3.1.0]hexane-6-carboxylic acid was stirred in 12 ml of 60% sulfuric acid (W/V%) at 145° C. for 4 days. After ice-cooling and neutralizing the reaction solution with 5 N aqueous solution of sodium hydroxide, it was purified by ion exchange chromatography (AG50W-X8 cation exchange resin (Bio-Rad), H+ type, eluent: water-50%THF/water-water-10%pyridine/water). The obtained crystals were washed with a mixture solution of tetrahydrofuran-water, yielding 41 mg of (1RS, 2SR, 5SR, 6SR)-2-amino-6fluoro-4oxobicyclo[3.1.0]hexane-2,6-dicarboxylic acid. The proton NMR and mass spectrograph data are shown below.

$^1$H-NMR(TFA-d)δ (ppm); 3.16 (1H, dd, J=4.6, 19.5 Hz), 3.45(1H, dd, J=4.6, 19.5 Hz), 3.46(1H, d, J=6.6 Hz), 3.67 (1H, d, J=6.6 Hz)

MS(ES) (nega)m/e; 216(M+–1)

Likewise, the following compounds were obtained from the lower polar diastereomer and the polar diastereomer of (1R*, 2S*, 5R*, 6S*)-2-spiro-5'-hydantoin-4,4-ethylenedithio-6-fluoro-N-((R)-1-phenylethyl) bicyclo [3.1.0]hexane-6-carboxyamide. The physical property data of each compound are shown below.

(-)-(1R*, 2S*, 5S*, 6S*)-2-amino-6-fluoro-4- oxobicyclo [3.1.0]hexane-2, 6-dicarboxylic acid m.p. 175° C. (decomposed)

$^1$H-NMR(TFA-d)δ (ppm); 3.16 (1H, dd, J=4.6, 19.5 Hz), 3.45(1H, dd, J=4.6, 19.5 Hz), 3.46(1H, d, J=6.6 Hz), 3.67 (1H, d, J=6.6 Hz) MS(ES) (nega) m/e; 216(M$^+$–1)

[α]D$^{26}$=–97.01(c=0.16, H$_2$O)

(+)-(1R*, 2S*, 5S*, 6S*)-2-amino-6fluoro-4-oxobicyclo [3.1.0]hexane-2, 6-dicarboxylic acid m.p. 175° C. (decomposed)

$^1$H-NMR(TFA-d)δ (ppm); 3.16 (1H, dd, J=4.6, 19.5 Hz), 3.45(1H, dd,

J=4.6, 19.5 Hz), 3.46(1H, d, J=6.6 Hz), 3.67(1H, d, J=6.6 Hz)

MS(ES) (nega) m/e; 216(M$^+$–1)

[α]D$^{26}$=+99.84(c=0.13, H$_2$O)

EXAMPLE –

Synthesis of (1RS, 2SR, 5RS, 6SR)-2-amino-4,4-ethylenedithio-6-fluorobicyclo[3.1.0]hexane-2, 6-dicarboxylic acid 120 mg of (1RS, 2SR, 5RS, 6SR)-2-spiro-5'-hydantoin-4,4-ethylenedithio-6-fluorobicyclo[3.1.0]hexane-6-carboxylic acid in 1.4 ml of 2 N aqueous solution of sodium hydroxide was treated under reflux for 1.5 days. After allowing to cool, it was purified by ion exchange chromatography (AG50W-X8 cation exchange resin (Bio-Rad), H$^+$ type, eluent: water-50%THF/water-water-10%pyridine/water), yielding 75 mg of (1RS, 2SR, 5RS, 6SR)-2-amino-4,4-ethylenedithio-6-fluorobicyclo [3.1.0]hexane-2,6-dicarboxylic acid. The physical property data are shown below. m.p. 230° C. (decomposed)

$^1$H-NMR(TFA-d)δ (ppm);3.07 (1H, dd, J=5.5, 16.1 Hz), 3.16(1H, d, J=5.5 Hz), 325(1H, dd, J=2.7, 7.1 Hz), 3.38–3.51(5H, m)

MS(ES) (Nega)m/e; 292(M$^{30}$–1, 100%)

EXAMPLE 15

Synthesis of (1RS, 2SR, 4SR, 5SR, 6SR) ethyl 2-spiro-5'-hydantoin-6-fluoro-4-hydroxybicyclo[3.1.0] hexane-6-carboxylate 1.3 g of (1RS, 4SR, 5SR, 6RS)ethyl 6-fluoro-4-hydroxy-2-oxobicyclo[3.1.0]hexane-6carboxylate was dissolved into 3.7 ml of ethanol. With ice-cooling, 3.7 ml of 1 N aqueous solution of sodium hydroxide was added dropwise thereto, and stirring was continued at this temperature for 15 min. After elevating the reaction solution's temperature up to room temperature, 860 mg of ammonium carbonate and 260 mg of potassium cyanide were added, and this was stirred at 37° C. for 3 days. After cooling the reaction mixture, the pH was adjusted to 1 by adding concentrated hydrochloric acid. This solution was treated by ion exchange chromatography (AG50W-X8 cation exchange resin (Bio-Rad), $H^+$ type, eluent: water), yielding 450 mg of crude (1RS, 2SR, 4SR, 5SR, 6SR)-2-spiro-5'-hydantoin-6-fluoro-4-hydroxybicyclo [3.1.0]hexane-6-carboxylic acid. 450 mg of this (1RS, 2SR, 4SR, 5SR, 6SR)-2-spiro-5'-hydantoin-6-fluoro-4-hydroxybicyclo [3.1.0]hexane-6-carboxylic acid, 90 mg of ethanol and 20 mg of 4-dimethylaminopyridine were dissolved into 3.9 ml of dimethylformamide. Further, 380 mg of 1(3-dimethylaminopropyl)-3ethylcarbodiimide hydrochloride was added thereto with ice-cooling, and this was stirred for one day. The reaction solution was poured into 1 N hydrochloric acid, extracted with chloroform six times, and dried over anhydrous sodium sulfate after consolidating the obtained organic layers. After filtering off the desiccant, the filtrate was concentrated under reduced pressure. The residue was purified by column chromatography (silica gel: MSG D75-60A (made by Dokai Chemicals Ltd.), eluent: ethyl acetate =50:1), yielding 198 mg of (1RS, 2SR, 4SR, 5SR, 6SR)ethyl 2-spiro-5'-hydantoin-6-fluoro-4-hydroxybicyclo[3.1.0]hexane-6-carboxylate. The proton NMR and mass spectrograph data are shown below.

$^1$H-NMR(DMSO-$d_6$)δ (ppm); 1.21 (3H, t, J=7.2 Hz), 1.90–2.08(2H, m), 2.26(1H, dd, J=1.8, 7.2 Hz), 2.45(1H, dd, J=1.8, 7.2 Hz), 4.17(2H, q, J=7.2 Hz), 4.33(1H, dd, J=5.6, 8.8 Hz), 4.75(1H, d, J=8.8 Hz), 8.13(1H, s), 11.00(1H, s)

MS(ES) (Nega)m/e; 271(M+−1, 100%)

EXAMPLE 16

Synthesis of (1RS, 2SR, 4SR, 5SR, 6SR)-2-amino-6-fluoro-4-hydroxybicyclo [3.1.0]hexane-2, 6-dicarboxylic acid 140 mg of (1RS, 2SR, 4SR, 5SR, 6SR) ethyl 2-spiro-5'-hydantoin-6-fluoro-4-hydroxybicyclo[3.1.0]hexane-6-carboxylate was stirred in 4 ml of 60% sulfuric acid (W/V %) at 145° C. for 2.5 days. After ice-cooling and neutralizing the reaction solution with 5 N aqueous solution of sodium hydroxide, this was purified by ion exchange chromatography (AG50W-X8 cation exchange resin (Bio-Rad), $H^{30}$ type, eluent: water-50%THF/water-water-10%pyridine/water). The obtained crystals were washed with a mixed solution of acetone-tetrahydrofuran, yielding 17 mg of (1RS, 2SR, 4SR, 5SR, 6SR)-2-amino-6-fluoro-4-hydroxybicyclo [3.1.0]hexane-2, 6-dicarboxylic acid. The physical property data are shown below. m.p. 220° C. (decomposed)

$^1$H_NMR(pyridine-$d_6$/$D_2$O=1/1)δ (ppm); 2.56–2.75(3H, m), 292(1H, dd, J=1.2, 6.9 Hz), 4.56(1H, d, J=5.4 Hz)

MS(ES) (Nega)m/e; 218(M$^+$−1, 100%)

Experimental Example (Effect of Test Compounds on cAMP Accumulation)

CHO cells stably expressing metabotropic glutamate receptors mG1uR2 were seeded in a 96-well plate (1.26*10$^4$ cells/well/0.32 cm$^2$/150 μl) in Dalbecco-modified Eagle medium [1% proline, 50 units/ml penicillin, 50 μg/ml streptomycin, 2 mMl-glutamine (added when used)] containing 10% dialyzed fetal bovine serum, and were cultured for 2 days at 37° C. under an atmosphere of 5% $CO_2$. After the medium was replaced with an L-glutamine free medium, they were cultured for 4 hours, and the supernatant liquid was aspirated. After adding 150 μl of PBS(+)-IBMX (10 mM PBS(−), 1 mM $MgCl_2$,1 mM $CaCl_2$, 1 mM IBMX), incubation was conducted at 37° C. under the presence of 5% $CO_2$ for 20 minutes. Once again the supernatant liquid was suctioned off, 60 μl of 10$^{-5}$ M Forskolin and PBS (+)-IBMX containing the specimens listed in Table 1 between 10$^{-10}$ and 10$^{-4}$ M were added, incubation was carried out for 15 minutes at 37° C. under the presence of 5% $CO_2$, and a study was carried out for the inhibitory effect of the agonists on the Forskolin stimulation cAMP accumulation quantity [for control, the conditions were set to Forskolin with no addition of the compounds (Tanabe et al., Neuron, 8, 169–179 (1992))]. The reactions were halted by adding 100 μl of ice-cooled ethanol, the entire quantity of the supernatant liquid was collected in a separate plate, then was dried up at normal temperature with an evaporator, and was kept at −20° C. In the dried-up samples, the quantity of cAMP was measured using a cAMP EIA kit (from the Amasham company). The control value was subtracted from each cAMP quantity. The concentration value of the test compounds at which the cAMP accumulation was inhibited 50% when stimulation was effected by 10$^{-5}$ M Forskolin was determined as $ED_{50}$. The results are presented in Table 1.

TABLE 1

| Test compound | $ED_{50}$ (nM) |
| --- | --- |
| Comp. 1 | 34.24 |
| Comp. 2 | 16.63 |
| Comp. 3 | 1.26 |
| Comp. 4 | 0.66 |
| Comp. 5 | 19.61 |
| LY354740 | 18.74 |
| Glutamate | 8770 |
| DCG IV | 98.28 |
| (1s,3R)-ACPD | 1500 |
| L-CCG-I | 121.04 |

Comp. 1:
(1RS, 2SR, 5RS, 6RS)-2-amino-6-fluorobicyclo[3.1.0] hexane-2,6-dicarboxylic acid
Comp. 2:
(−)-(1R*, 2S*, 5R*, 6R*)-2-amino-6-fluorobicyclo[3.1.0] hexane-2,6-dicarboxylic acid
Comp. 3:
(1RS, 2SR, 5SR, 6SR)-2-amino-6-fluoro-4-oxobicyclo [3.1.0]hexane-2,6-dicarboxylic acid
Comp. 4:
(+)-(1R*, 2S*, 5S*, 6S*)-2amino-6-fluoro-4-oxobicyclo [3.1.0]hexane-2,6-dicarboxylic acid
Comp. 5:
(1RS, 2SR, 4SR, 5SR, 6SR)-2-amino-6-fluoro-4-hydroxybicyclo [3.1.0]hexane-2, 6-dicarboxylic acid
LY354740:
(+)-(1S, 2S, 5R, 6S)-2-aminobicyclo [3.1.0]hexane-2, 6-dicarboxylic acid
DCG IV:
(2S, 1'R, 2'R, 3'R)-2-(2', 3'-dicarboxycycloproyl)glycine
(1S, 3R) ACPD:
(1S, 3R)-1-aminocyclopentane-1, 3-dicarboxylic acid
L-CCG-I:
(2S, 1'S, 2'S)-2-(carboxycyclopropyl)glycine

INDUSTRIAL APPLICABILITY

The 6-fluorobicyclo[3.1.0]hexane derivatives according to the present invention are useful as drugs. In particular, they are useful as agonists that act upon metabotropic glutamate receptors. Therefore, this invention can be used for the treatment and prevention of psychiatric disorders such as, for example, schizophrenia, anxiety and associated diseases, depression, bipolar disorder, and epliepsy, as well as neurological diseases such as, for example, drug dependence, cognitive disorders, Alzheimer's disease, Huntington's chorea, Parkinson's disease, dyskinesia associated with muscular stiffness, cerebral ischemia, cerebral failure, myelopathy, and head trauma.

What is claimed is:

1. A 6-fluorobicyclo[3.1.0]hexane derivative represented by the formula [I]

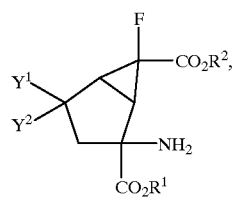

a pharmaceutically acceptable salt thereof, or a hydrate thereof.

2. The derivative according to claim 1, having a relative stereochemical configuration represented by the formulate [I']

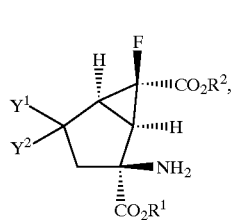

the pharmaceutically acceptable salt thereof, or the hydrate thereof.

3. The derivative according to claim 2, which is a (+) or (−)-(1R*, 2S*, 6S*)-2-amino-6-fluoro-4-substituted-bicyclo [3.1.0]hexane-2, 6-dicarboxylic acid, the pharmaceutically acceptable salt thereof, or the hydrate thereof.

4. The derivative according to claim 1, having a relative stereochemical configuration represented by the formula [II']

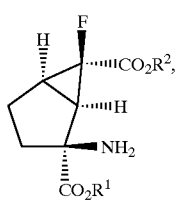

the pharmaceutically acceptable salt thereof, or the hydrate thereof.

5. The derivative according to claim 4, which is (−)-(1R*, 2S*, 5R*, 6R*)-2-amino-6-fluorobicyclo [3.1.0]hexane-2, 6-dicarboxylic acid, the pharmaceutically acceptable salt thereof, or the hydrate thereof.

6. The derivative according to claim 1, having a relative stereochemical configuration represented by the formula [III']

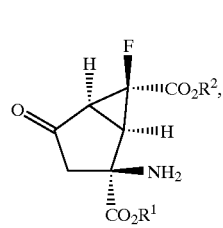

the pharmaceutically acceptable salt thereof, or hydrate thereof.

7. The derivative according to claim 6, which is (+)-(1R*, 2S*, 5S*, 6S*)-2-amino-6-fluoro-4-oxobicyclo [3.1.0] hexane-2, 6-dicarboxylic acid, the pharmaceutically acceptable salt thereof, or the hydrate thereof.

8. The derivative according to claim 1, having a relative stereochemical configuration represented by the formula [IV']

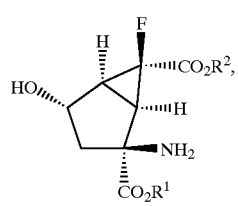

the pharmaceutically acceptable salt thereof, or the hydrate thereof.

9. The derivative according to claim 8, which is (+) or (−)-(1R*, 2S*, 4S*, 5S*, 6S*)-2-amino-6-fluoro-4-hydroxybicyclo [3.1.0]hexane-2, 6-dicarboxylic acid, the pharmaceutically acceptable salt thereof, or the hydrate thereof.

10. A pharmaceutical preparation that contains the compound according to claim 1, in combination with one or more members selected from pharmaceutically acceptable carriers, excipients, and diluents.

11. A drug which contains the compound according to claim 1 as an active ingredient.

12. The drug according to claim 11 that is a group 2 metabotropic glutamate receptor agonist.

13. The drug according to claim 11 that is an agent for the treatment or prevention of psychiatric disorders or neurological diseases.

* * * * *

UNITED STATES PATENT AND TRADEMARK OFFICE
CERTIFICATE OF CORRECTION

PATENT NO.    : 6,333,428 B1
DATED         : December 25, 2001
INVENTOR(S)   : Nakazato et al.

It is certified that error appears in the above-identified patent and that said Letters Patent is hereby corrected as shown below:

Column 2,
Line 16, "6position" should read -- 6-position --.

Column 3,
Line 4, "t-bytylthio" should read -- t-butylthio --.

Column 11,
Lines 1-10, which read:

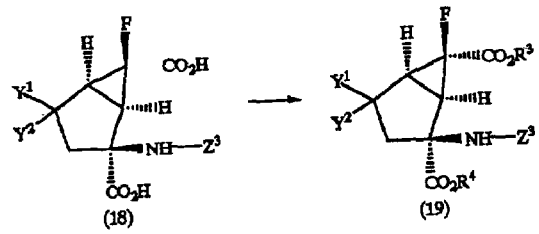

should read:

-- 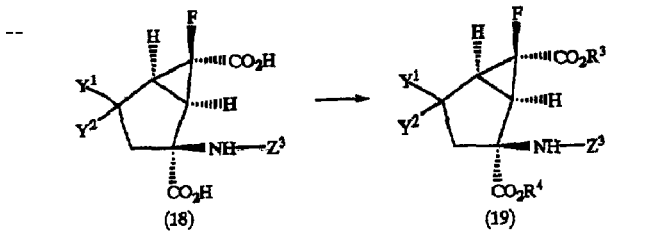

--

UNITED STATES PATENT AND TRADEMARK OFFICE
CERTIFICATE OF CORRECTION

PATENT NO. : 6,333,428 B1
DATED : December 25, 2001
INVENTOR(S) : Nakazato et al.

It is certified that error appears in the above-identified patent and that said Letters Patent is hereby corrected as shown below:

Column 15,

Line 17, "(CDCL$_3$)" should read -- (CDCl$_3$) --;

Line 24, "(CDCL$_3$)" should read -- (CDCl$_3$) --; and

Line 59, "(CDCL$_3$)" should read -- (CDCl$_3$) --.

Column 16,
Line 1, "(CDCL$_3$)" should read -- (CDCl$_3$) --;
Line 10, "(CDCL$_3$)" should read -- (CDCl$_3$) --;
Line 33, "(CDCL$_3$)" should read -- (CDCl$_3$) --;
Line 40, "CHCL$_3$)" should read -- CHCl$_3$) --;
Line 43, "(CDCL$_3$)" should read -- (CDCl$_3$) --;
Line 51, "CHCL$_3$)" should read -- CHCl$_3$) --; and
Line 61, "coolinyg" should read -- cooling --.

Column 18,
Line 44, "(CDCL$_3$)" should read -- (CDCl$_3$) --.

Column 19,
Line 7, "(CDCL$_3$)" should read -- (CDCl$_3$) --; and
Line 37, "(CDCL$_3$)" should read -- (CHCl$_3$) --.

Column 20,
Line 27, "(CDCL$_3$)" should read -- (CDCl$_3$) --; and
Line 56, "(CDCL$_3$)" should read -- CDCl$_3$) --.

Column 22,
Line 29, do not begin a new paragraph after "dd,";
Line 35, "EXAMPLE -" should read -- EXAMPLE 14 --; and
Line 55, "M$^{30}$" should read -- M$^+$ --.

UNITED STATES PATENT AND TRADEMARK OFFICE
CERTIFICATE OF CORRECTION

PATENT NO. : 6,333,428 B1
DATED : December 25, 2001
INVENTOR(S) : Nakazato et al.

It is certified that error appears in the above-identified patent and that said Letters Patent is hereby corrected as shown below:

Column 23,
Line 45, "$H^{30}$" should read -- $H^+$ --.

Column 24,
Line 35, "(1s,3R)-ACPD" should read -- (1S,3R)-ACPD --.

Column 25,
Line 22, before "a pharmaceutically" insert the following:

-- wherein R' and $R^2$ are the same or different and each represents a hydrogen atom, a $C_{1-10}$ alkyl group, a $C_{3-8}$ cycloalkyl group or a $C_{3-8}$ cycloalkyl-$C_{1-5}$ alkyl group: $Y^1$ and $Y^2$ are the same or different and each represents a hydrogen atom, a $C_{1-10}$ alkylthio group, a $C_{3-8}$ cycloalkylthio group, a $C_{3-8}$ cycloalkyl-$C_{1-5}$ alkylthio group, a $C_{1-5}$ alkoxy group, a $C_{3-8}$ cycloalkoxy group or a $C_{3-8}$ cycloalkyl-$C_{1-5}$ alkoxy group; or one of $Y^1$ and $Y^2$ represents a hydrogen atom and the other represents a hydroxyl group, a $C_{1-5}$ alkoxy group, a $C_{3-8}$ cycloalkoxy group or a $C_{3-8}$ cycloalkyl-$C_{1-5}$ alkoxy group; or $Y^1$ and $Y^2$ together represent an oxygen atom or -X(CH$_2$)$_n$X- (X represents an oxygen atom or a sulfur atom: n is 2 or 3), --;

Column 25,
Line 38, before "a pharmaceutically acceptable" insert the following:
-- wherein $R^1$ and $R^2$, and $Y^1$ and $Y^2$ are the same as in the case of the formula [I], --; and
Line 58, before "the pharmaceutically" insert -- wherein $R^1$ and $R^2$ are the same as in the case of the formula [I], --.

UNITED STATES PATENT AND TRADEMARK OFFICE
CERTIFICATE OF CORRECTION

PATENT NO. : 6,333,428 B1
DATED : December 25, 2001
INVENTOR(S) : Nakazato et al.

It is certified that error appears in the above-identified patent and that said Letters Patent is hereby corrected as shown below:

Column 26,
Line 19, before "the pharmaceutically" insert -- wherein $R^1$ and $R^2$ are the same as in the case of the formula [I], --; and
Line 40, before "the pharmaceutically" insert -- wherein $R^1$ and $R^2$ are the same as in the case of the formula [I], --.

Signed and Sealed this

Sixteenth Day of July, 2002

Attest:

JAMES E. ROGAN
Attesting Officer    Director of the United States Patent and Trademark Office